(12) United States Patent  
Jones et al.

(10) Patent No.: US 8,834,474 B2  
(45) Date of Patent: Sep. 16, 2014

(54) SINGLE ACTION ANTI-TORQUE ROD REDUCER

(75) Inventors: Scott A Jones, McMurray, PA (US); Andy Rock, Spring Grove, PA (US)

(73) Assignee: K2M, Inc., Leesburg, VA (US)

( * ) Notice: Subject to any disclaimer, the term of this patent is extended or adjusted under 35 U.S.C. 154(b) by 324 days.

(21) Appl. No.: 12/852,633

(22) Filed: Aug. 9, 2010

(65) Prior Publication Data

US 2010/0324609 A1    Dec. 23, 2010

Related U.S. Application Data

(63) Continuation of application No. 11/514,915, filed on Sep. 5, 2006, now Pat. No. 7,771,430.

(60) Provisional application No. 60/721,481, filed on Sep. 29, 2005.

(51) Int. Cl.  
    *A61B 17/70*    (2006.01)

(52) U.S. Cl.  
    CPC ........ *A61B 17/7086* (2013.01); *A61B 17/7032* (2013.01); *A61B 17/7091* (2013.01)  
    USPC ...................................... 606/86 A

(58) Field of Classification Search  
    USPC ............... 606/86 A, 86 R, 99, 104, 246, 279; 81/442, 444, 451–455; 135/114, 135/120.1–120.3, 907; 294/100  
    See application file for complete search history.

(56) References Cited

U.S. PATENT DOCUMENTS

| | | | |
|---|---|---|---|
| 2,248,054 A | 7/1941 | Becker | |
| 3,604,487 A | 9/1971 | Gilbert | |
| 5,020,519 A | 6/1991 | Hayes et al. | |
| 5,466,243 A | 11/1995 | Schmieding et al. | |
| 5,910,141 A | 6/1999 | Morrison et al. | |
| 6,416,521 B1 | 7/2002 | Waldner et al. | |
| 6,440,133 B1 * | 8/2002 | Beale et al. ................ | 606/86 A |
| 6,648,888 B1 * | 11/2003 | Shluzas ...................... | 606/86 A |
| 6,660,006 B2 * | 12/2003 | Markworth et al. ........ | 606/86 A |
| 6,790,209 B2 | 9/2004 | Beale et al. | |
| 7,909,835 B2 * | 3/2011 | Oribe et al. .................. | 606/104 |
| 2002/0095153 A1 * | 7/2002 | Jones et al. .................... | 606/61 |
| 2003/0225408 A1 | 12/2003 | Nichols et al. | |
| 2004/0215190 A1 | 10/2004 | Nguyen et al. | |
| 2005/0143749 A1 | 6/2005 | Zalenski et al. | |
| 2005/0149053 A1 | 7/2005 | Varieur et al. | |
| 2005/0192587 A1 | 9/2005 | Lim | |
| 2005/0192589 A1 | 9/2005 | Raymond et al. | |
| 2005/0261702 A1 * | 11/2005 | Oribe et al. .................. | 606/103 |
| 2006/0036260 A1 | 2/2006 | Runco et al. | |

(Continued)

*Primary Examiner* — Eduardo C. Robert  
*Assistant Examiner* — Steven Cotroneo  
(74) *Attorney, Agent, or Firm* — Carter, DeLuca, Farrell & Schmidt, LLP

(57) ABSTRACT

Provided is a novel rod reducing device for use in spinal fixation procedures. The device is capable with a single action of securely grasping the head of a bone screw while reducing a connecting rod into the head of the bone screw and while in position on the bone screw provide a cannula access for a bone screw locking cap and tightening instrument and securing the bone screw during the tightening of the locking cap so as to provide an anti-torque effect. The device is also capable of releasing from the bone screw with a reversal of the single action used to activate the device. A method of using the device and a kit wherein the device is one component is also provided.

16 Claims, 8 Drawing Sheets

(56) References Cited

U.S. PATENT DOCUMENTS

| | | |
|---|---|---|
| 2006/0074418 A1 | 4/2006 | Jackson |
| 2006/0089651 A1 | 4/2006 | Trudeau et al. |
| 2006/0200132 A1 | 9/2006 | Chao et al. |
| 2007/0213722 A1 | 9/2007 | Jones et al. |
| 2008/0172062 A1 | 7/2008 | Donahue et al. |

* cited by examiner

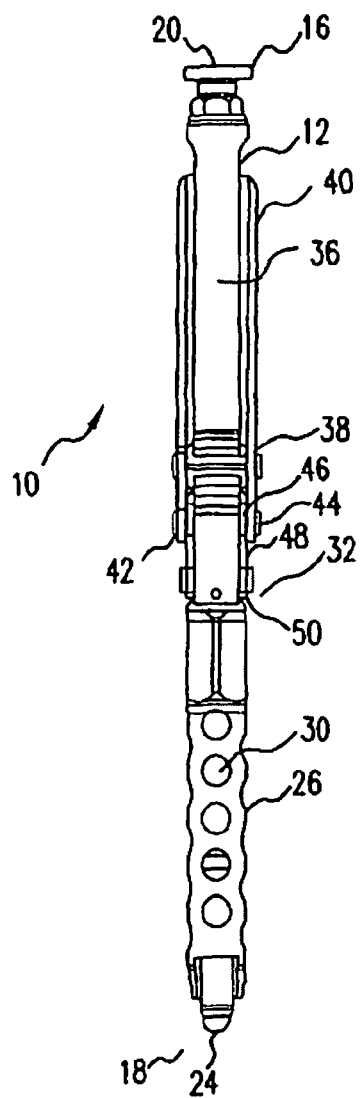
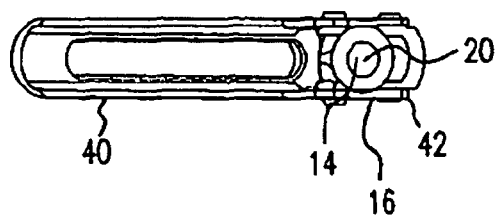
FIG.5
FIG.4

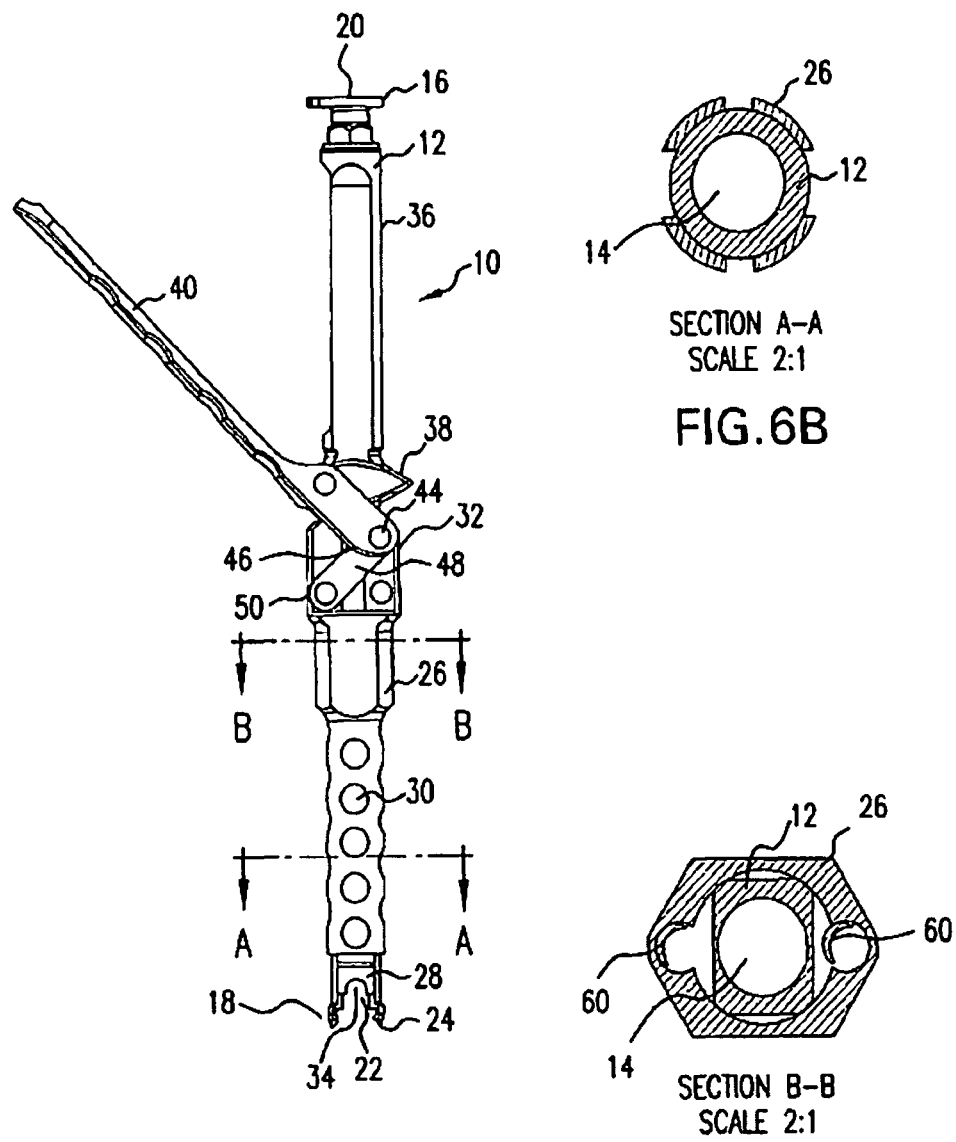

SECTION A-A

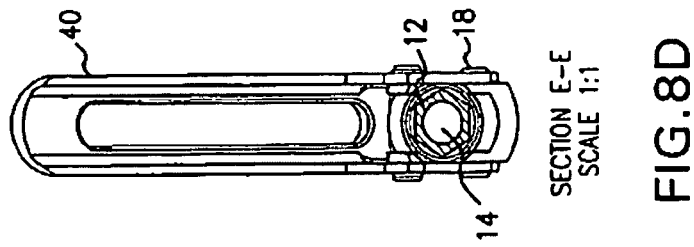
FIG. 8D SECTION E-E SCALE 1:1
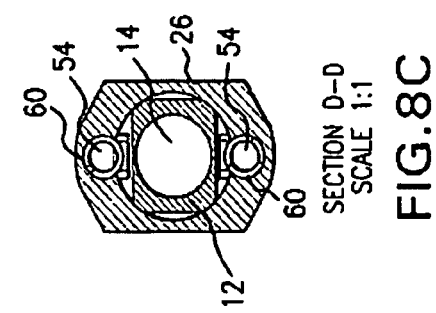
FIG. 8C SECTION D-D SCALE 1:1
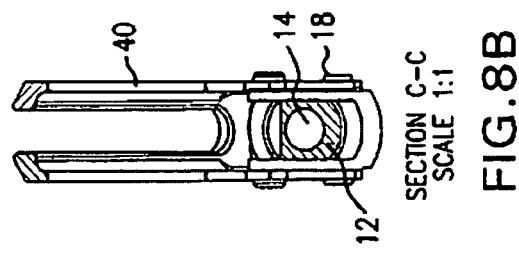
FIG. 8B SECTION C-C SCALE 1:1
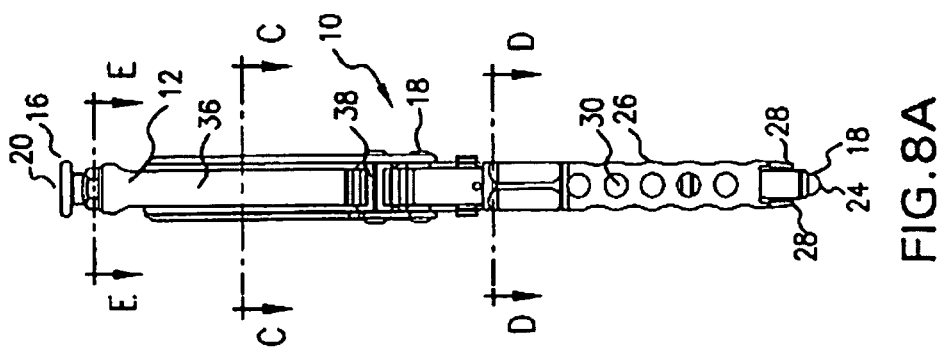
FIG. 8A

SINGLE ACTION ANTI-TORQUE ROD REDUCER

CROSS-REFERENCE TO RELATED APPLICATIONS

This application is a continuation of U.S. patent application Ser. No. 11/514,915, filed on Sep. 5, 2006, which claims priority to U.S. Provisional Patent Application Ser. No. 60/721,481, filed on Sep. 29, 2005. The priority of these prior applications is expressly claimed and their disclosures are hereby incorporated by reference in their entirety.

BACKGROUND

1. Technical Field

The present invention relates to orthopedic surgery, and in particular to devices for stabilizing and fixing the bones and joints of the body. Particularly, the present invention relates to an instrument capable of reducing a spinal rod into position in a rod receiving notch in the head of a bone screw and holding the same in position and providing anti-torque effect on the bone screw while a bone screw locking cap is attached to the head of the bone screw.

2. Description of Related Art

The spinal column is a complex system of bones and connective tissues that provides support for the human body and protection for the spinal cord and nerves. The adult spine is comprised of 24 vertebral bodies, which are subdivided into three areas including seven cervical vertebrae, 12 thoracic vertebrae and five lumbar vertebrae. Between each vertebral body is an intervertebral disc that cushions and dampens the various translational and rotational forces exerted on the spinal column.

There are various disorders, diseases and types of injury which the spinal column may experience in a lifetime. The problems may include but are not limited to scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure known as spinal fusion. A spinal fusion procedure involves fusing two or more vertebral bodies in order to eliminate motion at the intervertebral disc or joint. To achieve this, natural or artificial bone, along with a spacing device, replaces part or all of the intervertebral disc to form a rigid column of bone, which is stabilized by mechanical hardware.

The mechanical hardware used to immobilize the spinal column typically involves a series of bone screws and metal rods or plates. When the spine surgery is posteriorly performed, it is common practice to place bone screws into the vertebral bodies and then connect a metal rod between the bone screws thus creating a rigid structure between adjacent vertebral bodies. When the spine surgery is performed anteriorly, it is common practice to attach a thin metal plate directly to the vertebral bodies and secure it to each vertebral level using one or more bone screws.

The process of properly inserting the spinal rod into the receiving slot of a bone screw and then securing that connecting rod in place often can require that the surgeon use a number of instruments and expend a great deal of time and effort to accomplish the task. When bone screws in several adjacent vertebra are to securely connected by a spinal rod, the repeated process of inserting the rod into the heads of the bone screws aid then securing the rod in place for each respective bone screw can be difficult, tiresome and time consuming. It is therefore important that an instrument be provided that is specifically designed to facilitate the process for the surgeon such that the connecting rod can be easily and quickly inserted into each bone screw and with minimal effort and loss of time. It is further important that the bone screws be held in a stable configuration to avoid the application of additional torque to the screw and the bone into which the screw is inserted when the locking cap is secured into position.

Conventional efforts to meet this need have fallen short in that no single instrument has been provided that effectively positions and inserts a connecting rod into position in the receiving slot of the head of a bone screw and also provides a stable anti-torque effect during the attachment of a bone screw locking cap to the head of each respective bone screw.

For these reasons there remains a need for a device which, in one simple action such as squeezing a lever, can reduce a posteriorly introduced rod into the head of a bone screw and provide an anti-torque effect to the bone screw while a bone screw locking cap is secured to the bone screw.

SUMMARY

In accordance with an embodiment of the present disclosure, there is provided a rod reducing device for reducing a rod into a head of a bone screw. The device includes a housing, a sleeve and an actuation assembly. The housing defines a longitudinal axis and a lumen extending longitudinally within the housing. The sleeve at least partially slidably encloses the housing. The actuation assembly includes a lever pivotally mounted to the housing about a first pivot and a cam member pivotally mounted to the sleeve about a second pivot. The lever and the cam member are pivotally connected about a third pivot. The lever is movable between a first position in which the lever is outwardly extended from the housing to a second position in which the lever is aligned with the housing. The third pivot opposes the first and second pivots with respect to the longitudinal axis when the lever is in the first position. Moreover, actuation of the lever between the first and second positions causes reciprocating translation of the sleeve along the longitudinal axis.

In an embodiment, the third pivot may be distal of the first pivot on the lever and proximal of the second pivot on the cam member. In addition, the sleeve may include a connecting rod drive member configured to engage the rod. The connecting rod drive member may include a concavity corresponding to the shape of the rod.

In another embodiment, the housing may include a grasping element at a distal end of the housing. The grasping element is configured to securely retain the head of the bone screw. The grasping element may be a pair of opposing members. Furthermore, the grasping element may be longitudinally tapered with respect to the thickness thereof, whereby a distal translation of the sleeve moves the grasping element toward the longitudinal axis to securely engage the head of the bone screw. The grasping element may also extend out of a distal end portion of the sleeve.

In still another embodiment, the lumen of the housing may be dimensioned to receive a bone screw locking cap and an instrument for positioning the locking cap in the bone screw. Moreover, the device may further include a hand guard disposed proximal of the sleeve, as well as a biasing member to urge the lever to the first position.

In accordance with another embodiment of the present disclosure, there is provided a surgical device including a housing defining a lumen therein, a sleeve slidably disposed in the lumen of the housing, a rod engaging portion disposed at a distal end of the sleeve, a biasing member operably coupling the sleeve and the housing, and an actuation lever pivotably coupled to the housing. The actuation lever is pivotable with respect to the housing such that when the actuation lever is substantially parallel with the housing, the sleeve translates distally with respect to the housing and the biasing member is longitudinally compressed, and when the actuation lever defines an acute angle with respect to the housing, the biasing member urges the sleeve proximally with respect to the housing.

In an embodiment, the sleeve may further include a grasping element that is adapted for releasably coupling to a screw. A distal movement of the rod engaging portion may urge a rod into a head of the screw.

In still another embodiment, an instrument may be insertable through the lumen of the housing when the grasping element is coupled to the screw. In addition, the surgical device may include a locking device operable by the instrument.

BRIEF DESCRIPTION OF THE DRAWINGS

The foregoing and other features of the disclosed embodiments will become apparent to one skilled in the art, relates upon consideration of the following description, with reference to the accompanying drawings, wherein:

FIG. 4 shows a back view of the device shown in FIG. 3A.

FIG. 5 shows a top view of the device shown in FIG. 3A;

FIGS. 6A-C show transverse cross-sectional views of the device in the open and unlocked configuration from a side view;

FIGS. 8A-D show the device in the closed and locked configuration from a back view (FIG. 8A), a proximal cross-section (FIG. 8B), a mid-section cross-section of the same in FIG. 8C, and an extreme proximal cross-section the anti-torque connection point (FIG. 8D).

DETAILED DESCRIPTION OF PREFERRED EMBODIMENTS

Detailed embodiments are disclosed herein; however, it is understood that the following description is provided as being exemplary of the invention, which may be embodied in various forms without departing from the scope of the claimed invention. Thus, the specific structural and functional details provided in the description are non-limiting, but serve merely as a basis for the invention defined by the claims provided herewith.

Figure 1:
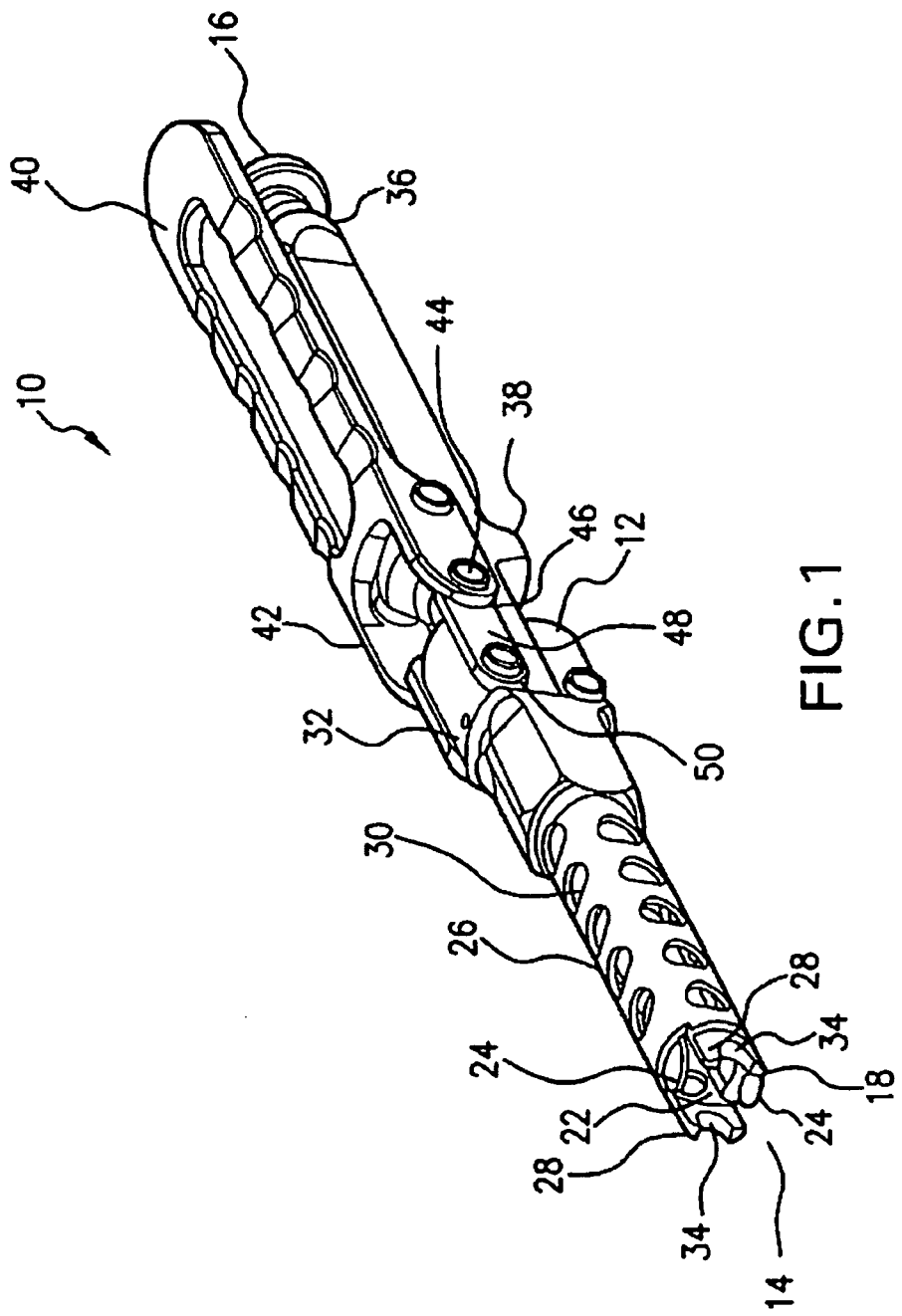
FIG. 1 shows an isometric view of the device.
Figure 2:
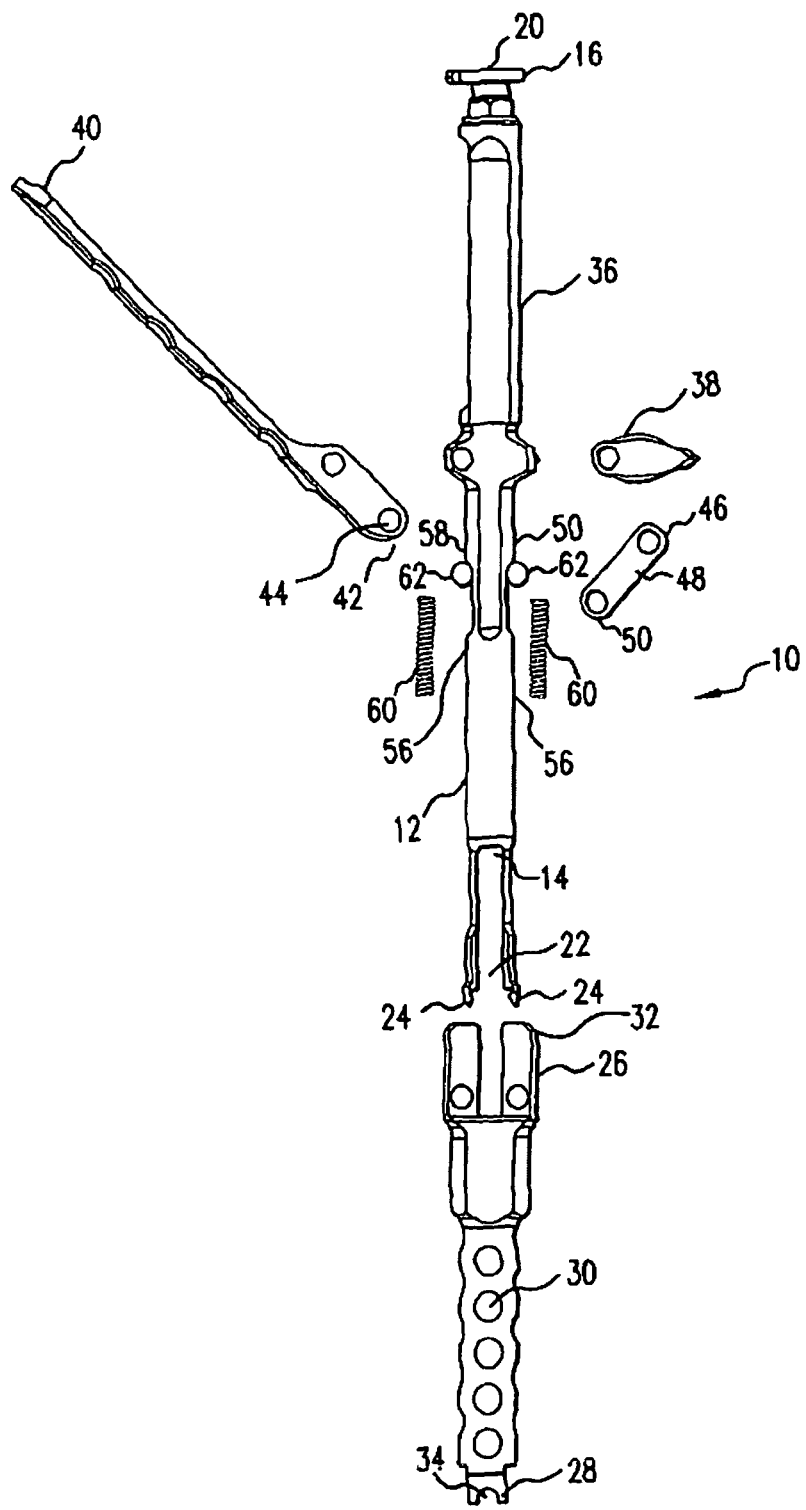
FIG. 2 is an exploded view showing the components of the device.
Figures 3A, 3B:
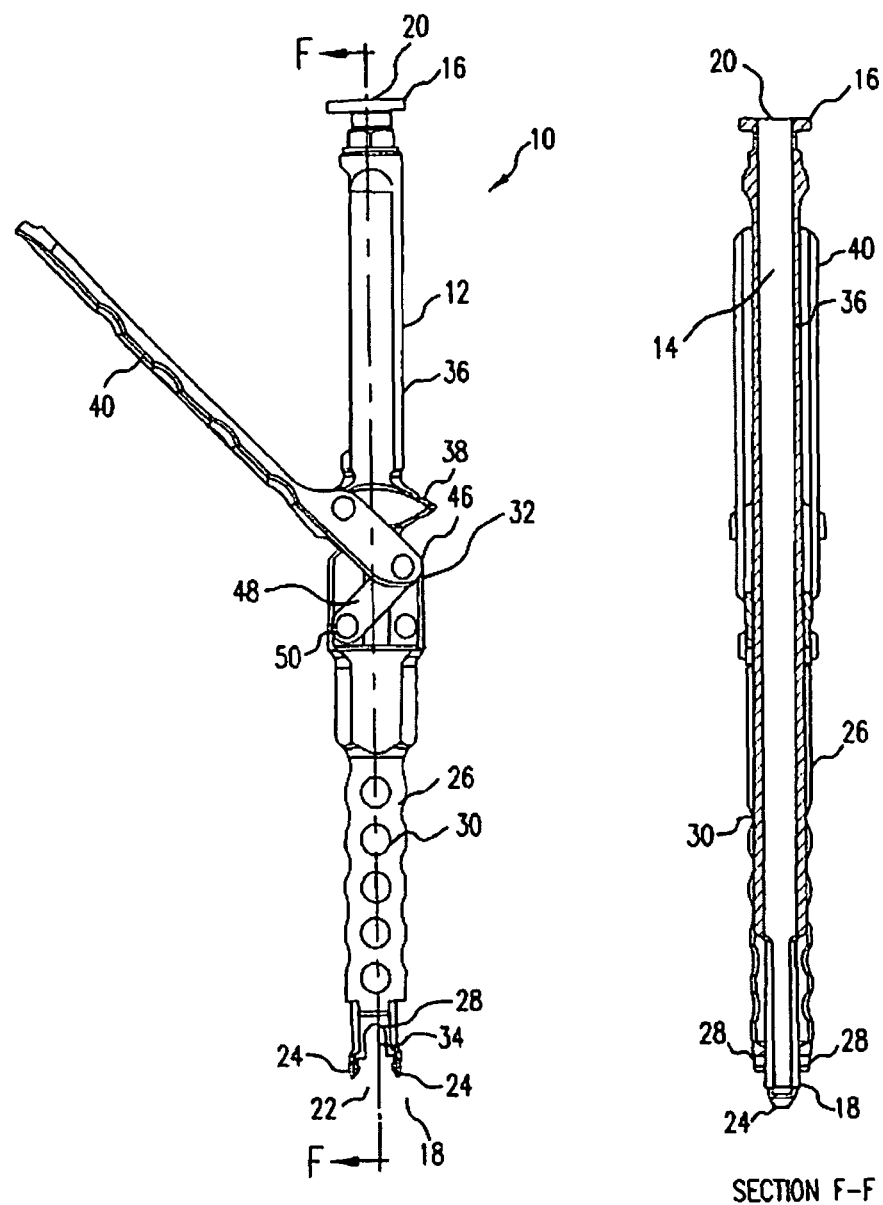
FIG. 3A-B show the device in the open and unlocked configuration from a side view as shown in FIG. 3A and a longitudinal cross-section of the same in FIG. 3B.
Figure 7B:
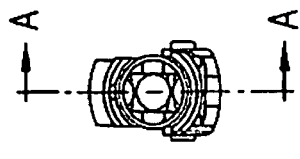
FIGS. 7A-D show the device in a closed and locked configuration; specifically shown in FIG. 7A is a side view of the device, in FIG. 7B is an end view of the device, in FIG. 7C is cross-section A-A of the device, and in FIG. 7D is a front view of the device.
Figure 7A:
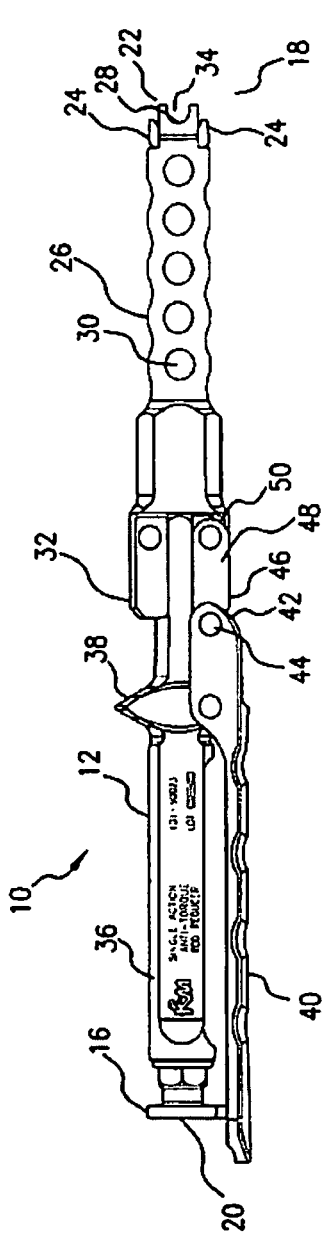
Figure 7C:
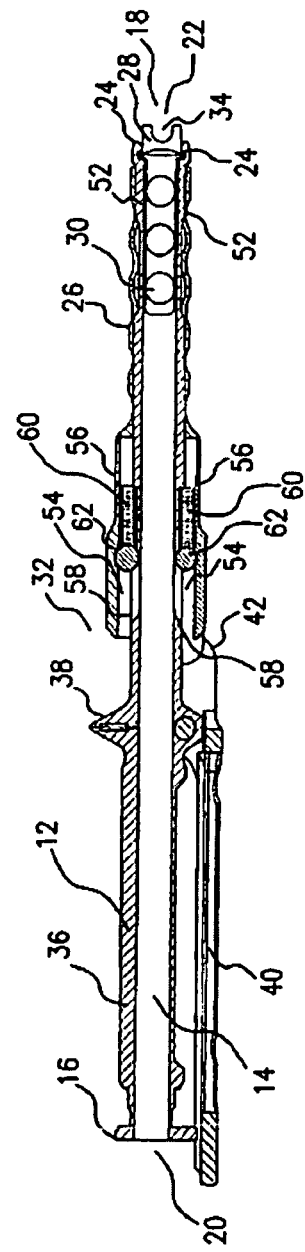
Figure 7D:
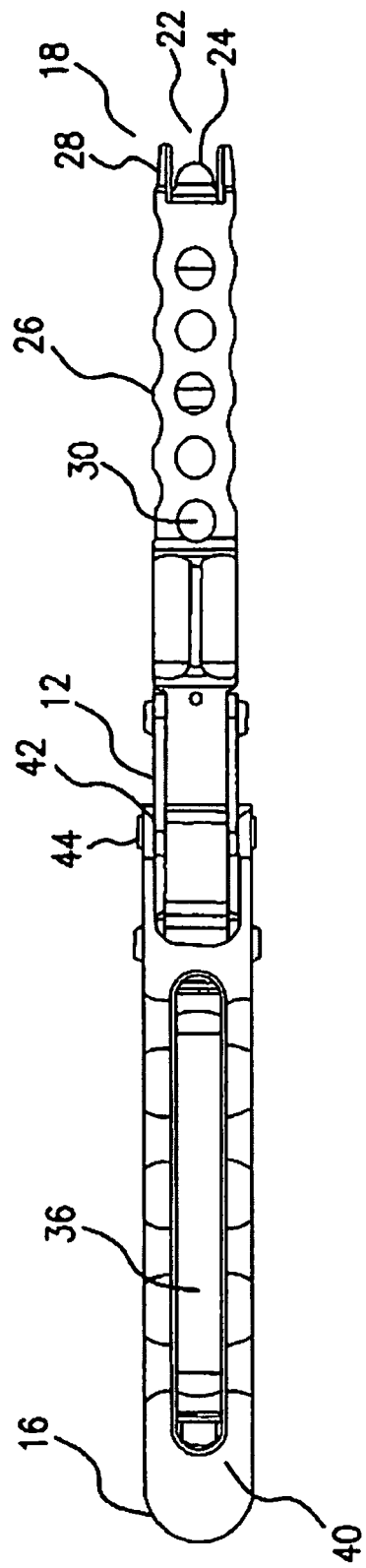

FIGS. 1-8 illustrate an example of a cannulated connecting rod reducing device, generally shown at 10, which, in one simple action such as squeezing a lever, can reduce a posteriorly introduced rod into a receiving slot in the head of a bone screw and then provide an anti-torque effect to the bone screw while a bone screw locking cap introduced through the cannula of the device is secured to the bone screw.

As shown in FIGS. 1-8 the cannulated rod reducing device 10 is an elongated surgical instrument having a device housing 12 that defines a device lumen 14, which extends from the device proximal or first end 16 to the full length of device 10 exiting from the device housing 12 at the device distal or second end 18. The proximal opening 20 of the lumen 14, as defined by the first end 16 of the housing 12, is sized and configured to receive and allow free passage of a bone screw locking cap and an instrument for positioning and tightening the locking cap securely into place in the locking cap receptacle of a bone screw. The first end 16 of the device is configured to facilitate the selective, releasable attachment of an anti-torque handle, which can be of any conformation suitable to facilitate manual grasping and application of anti-torque force to the device. The lumen 14 and the exit portal 22 defined by the second end 18 of the housing 12 are similarly sized and configured to allow free passage of a bone screw locking cap and the associated tightening instrument. The housing 12 at the exit portal 22 is configured to provide bone screw grasping elements 24, which are designed to securely grasp and hold the head of a bone screw. Preferably, the grasping elements 24 are configured as a pair of opposing elements; however, other configurations for the grasping elements are within the concept of the invention.

Circumferentially and slidably disposed around a lower portion of the housing is a sleeve 26 that extends to a position proximate to the second end 18 of the housing 12. The sleeve 26 at the second end 18 of the housing 12 is configured to form a connecting rod driving member 28. The sleeve 26 can be formed with perforations 30 to reduce the overall weight of the device but must have sufficient compressive strength to be capable of transferring force applied at the proximal end of the sleeve 32. To facilitate contact with a connecting rod, the driving member 28 can be configured with a shape that is complementary to that of the connecting rod with which it will come into contact during operation. Preferably, the grasping member 28 will generally define a concavity 34; however, any shape that is complementary to the shape of the connecting rod will be within the concept of the invention.

The proximal portion of the device 10 is provided with a handle 36. To facilitate operation of the device and improve the grip on the device by the user, a hand guard 38 can be provided on the housing 12 at a position above the proximal end 32 of the sleeve 26. An actuation lever 40 is pivotally mounted to housing 12 at a position above the sleeve 26 and approximately adjacent to the hand guard 38. The distal end 42 of the actuation lever 40 is pivotally connected to a second pivot point 44, which is also pivotally connected to a first end 46 of a force transfer arm 48. The second end 50 of the force transfer arm 48 is pivotally connected to the proximal end 32 of the sleeve 26. The combination of the actuation lever 40 pivotally connected to the force transfer arm 48, which in turn is pivotally connected to the sleeve 26 functions in a scissor-jack manner as is well known in the art. As shown in a comparison of FIG. 3A, the device in an open configuration, and FIG. 8A, the device in a closed configuration, the inward pivotal movement of the actuation lever 40 toward the handle 36 creates a scissor-jack transfer of force which acts to slidably move the sleeve 26 distally along the outside of the housing 12 to a position where the rod driving member 28 can contact and reduce a connecting rod into the head of a bone screw. As shown in FIGS. 1-8, the device 10 is configured to preferably reduce a connecting rod into the head of a bone screw form a position directly above the bone screw. The action of reducing the rod into the head of a bone screw is facilitated by the grasping elements 24 at the second end 18 of the housing 12 securely holding the bone screw in place relative to the device 10. As shown in FIG. 8C, the housing 12 proximate to the second end 18 and the grasping elements 24 is thickened to form a cam surface 52. As the sleeve 26 is forced distally over the cam surface 52 of the housing 12, the grasping elements 24 are forced inward so as to engage the head of a bone screw and securely hold the same.

The device can be provided with a biasing element compartment 54 that is defined as a space between a portion of the sleeve 26 and an adjacent portion of the housing 12. The compartment 54 is limited at a distal position by a biasing element stop 56 and limited at a proximal position by a retaining member stop 58. A biasing element 60 is contained within the compartment 54, the biasing element 60 is capable of compression under force and capable of expansion upon removal of the force. The biasing element 60 is preferably a coil spring and more preferably a Lee Spring that is sized to fit when fully expanded within the compartment. Within the compartment 54 and positioned above the biasing element 60 is a retaining member 62. When the actuation lever 40 is squeezed inward toward the housing 12, the pivotal action of the lever 40 and the force transfer arm 48 serves to slidably move the sleeve 26 downward along the outside of the housing 12. As the sleeve 26 moves downward, the retaining member stop 58, in contact with the retaining member 62, transfers compression force against the biasing element 60 causing it to compress against the biasing element stop 56. This compression of the biasing element 60 is only relieved when the actuation lever 40 is moved outward from the housing 12 and the relief of that compression forces serves to pull the sleeve 26 back upward along the housing and away from the second end 18 of the housing 12.

In use, a surgeon accesses the patient's spine in a known manner either using open surgical techniques or minimally invasive techniques, and prepares the bone to receive screws, as is deemed appropriate under the circumstances. Multiple screws can be inserted into bone according to the operative plan of the surgeon, and a rod is placed in or adjacent to the rod receiving recess of each respective screw. The surgeon then uses the device to position the connecting rod in the receiving portion of the head of a first screw, after which, a bone screw locking cap is positioned in the head of the bone screw through the cannula lumen 14 of the device using an appropriate instrument. The bone screw is securely held by the device 10 so as to provide an anti-torque effect as torque is applied to the locking cap by a tightening instrument inserted through the cannula lumen 14. The device 10 is then released from the screw by a reversal of the movement of the actuation lever 40. The plurality of screws can each, in turn, be attached to a connecting rod using the device 10. In the event of revision surgery, the device 10 can be used to securely hold the bone screw in place and provide anti-torque while the locking cap can be removed through the cannula lumen 14 of the device 10.

The materials used to construct the present invention are those which have sufficient strength, resiliency, and biocompatability as is well known in the art for such devices. Methods of manufacture of such surgical implant devices is also well known in the art. By way of example only, suitable materials for screw 3 include titanium, titanium alloys including Nitinol, stainless steel, and cobalt chrome alloys. The device is intended to be cleaned, re-sterilized and used in multiple procedures, and so may be made of stainless steel or other suitable materials for this purpose. Because the device is not intended to be implanted in the body, implant grade materials are not required and the additional expense for such materials may not be justified; however, such materials may be used if desired.

It is contemplated to provide the device 10 as a component of a kit that can include at least one bone screw, at least one connecting rod, at least one bone screw locking cap and the device 10. Additional devices such as cross-connectors, hooks or links can also be included in the kit.

Each of the embodiments described above are provided for illustrative purposes only and it is within the concept of the invention to include modifications and varying configurations without departing from the scope of the invention that is limited only by the claims included herewith.

What is claimed is:

1. A rod reducing device for reducing a rod into a head of a bone screw, the device comprising:
   a housing defining a longitudinal axis and a lumen extending longitudinally within the housing;
   a sleeve engaging at least a portion of the housing, the sleeve slidable relative to the housing along the longitudinal axis; and
   an actuation assembly including:
      a lever pivotally mounted to the housing about a first pivot; and
      a cam member pivotally mounted to the sleeve about a second pivot, the lever and the cam member being pivotally connected about a third pivot, the lever being movable between a first position in which the first and second pivots are adjacent a first lateral side of the rod reducing device and the third pivot is adjacent a second lateral side of the rod reducing device and a second position in which the first, second, and third pivots are longitudinally aligned in a common plane, wherein actuation of the lever between the first and second positions causes reciprocating translation of the sleeve along the longitudinal axis to effect reduction of the rod into the head of the bone screw.

2. The rod reducing device according to claim 1, wherein the third pivot is distal of the first pivot on the lever.

3. The rod reducing device according to claim 2, wherein the third pivot is proximal of the second pivot on the cam member.

4. The rod reducing device according to claim 1, wherein the sleeve includes a connecting rod drive member configured to engage the rod.

5. The rod reducing device according to claim 4, wherein the connecting rod drive member includes a concavity corresponding to the shape of the rod.

6. The rod reducing device according to claim 1, wherein the housing includes a grasping element at a distal end of the housing, the grasping element configured to securely retain the head of the bone screw.

7. The rod reducing device according to claim 6, wherein the grasping element is a pair of opposing members.

8. The rod reducing device according to claim 6, wherein the grasping element is longitudinally tapered with respect to the thickness thereof, whereby a distal translation of the sleeve moves the grasping element toward the longitudinal axis to securely engage the head of the bone screw.

9. The rod reducing device according to claim 6, wherein the grasping element extends out of a distal end portion of the sleeve.

10. The rod reducing device according to claim 1, wherein the lumen of the housing is dimensioned to receive a bone screw locking cap and an instrument for positioning the locking cap in the bone screw.

11. The rod reducing device according to claim 1, further comprising a hand guard disposed proximal of the sleeve.

12. The rod reducing device according to claim 1, further comprising a biasing member to urge the lever to the first position.

13. The rod reducing device according to claim 1, wherein the lever includes a distal portion distal of the first pivot, the distal portion movable between the first and second lateral sides of the rod reduction device.

14. The rod reducing device according to claim 1, wherein the first lateral side is spaced apart from the second lateral side.

15. The rod reducing device according to claim 1, wherein the housing includes first and second lateral sides on opposite sides of the housing, wherein when the lever is in the first position the first and second pivots are adjacent the first lateral side of the housing and the third pivot is adjacent the second lateral side of the housing.

16. A rod reducing device for reducing a rod into a head of a bone screw, the device comprising:
  a housing defining a longitudinal axis and a lumen extending longitudinally within the housing, the housing including a grasping element at a distal end of the housing, the grasping element configured to securely retain the head of the bone screw;
  a sleeve at least partially slidably enclosing the housing; and
  an actuation assembly including:
    a lever pivotally mounted to the housing about a first pivot; and
    a cam member pivotally mounted to the sleeve about a second pivot, the lever and the cam member being pivotally connected about a third pivot, the lever being movable between a first position in which the first and second pivots are adjacent a first lateral side of the rod reducing device and the third pivot is adjacent a second lateral side of the rod reducing device and a second position in which the first, second, and third pivots are longitudinally aligned in a common plane, wherein actuation of the lever between the first and second positions causes reciprocating translation of the sleeve along the longitudinal axis to effect reduction of the rod into the head of the bone screw, wherein the grasping element is longitudinally tapered with respect to the thickness thereof, whereby a distal translation of the sleeve moves the grasping element toward the longitudinal axis to securely engage the head of the bone screw.

* * * * *